United States Patent [19]

Finney

[11] 4,378,792
[45] Apr. 5, 1983

[54] PENILE PROSTHESIS
[75] Inventor: Roy P. Finney, Tampa, Fla.
[73] Assignee: Medical Engineering Corporation, Racine, Wis.
[21] Appl. No.: 313,729
[22] Filed: Oct. 22, 1981

Related U.S. Application Data

[62] Division of Ser. No. 150,231, May 15, 1980, Pat. No. 4,318,396.

[51] Int. Cl.³ ............................................. A61F 5/00
[52] U.S. Cl. ........................................... 128/79; 3/1
[58] Field of Search ................................ 128/79; 3/1

[56] References Cited
U.S. PATENT DOCUMENTS

| 3,954,102 | 5/1976 | Buuck | 128/79 |
| 4,224,934 | 9/1980 | Scott et al. | 128/79 |
| 4,235,227 | 11/1980 | Yamanaka | 128/79 |
| 4,267,829 | 5/1981 | Burton et al. | 128/79 |

Primary Examiner—Stephen C. Pellegrino
Attorney, Agent, or Firm—Quarles & Brady

[57] ABSTRACT

A penile erectile system which is adapted to be surgically implanted in man for the treatment of erectile impotence includes an elongated penile implant adapted to be implanted in the corpus cavernosum of a penis, said member including a stem at one end, a tip at the other end, and first and second internal chambers separated by a dividing wall, said chambers being axially positioned between the stem and tip, the first chamber having a resilient collapsible side wall and the second chamber having a flexible non-distensible side wall. Both of the chambers are normally substantially filled with fluid and are connected by an open passage which extends through the dividing wall which permits fluid to flow between the first and the second chambers. The second non-distensible chamber is pressurized by moving the dividing wall towards the stem and maintaining it in that position thus collapsing the first chamber and forcing pressurizing fluid from the first into the second chamber.

3 Claims, 11 Drawing Figures

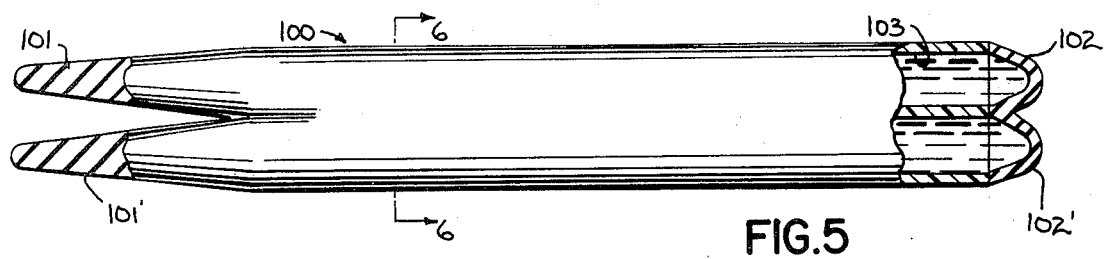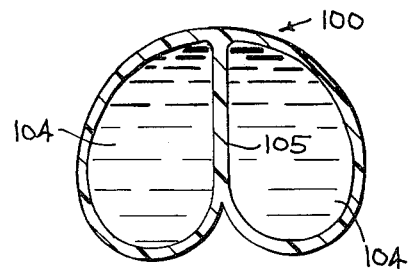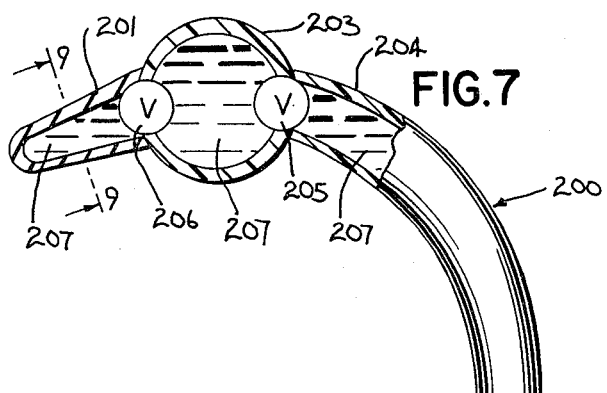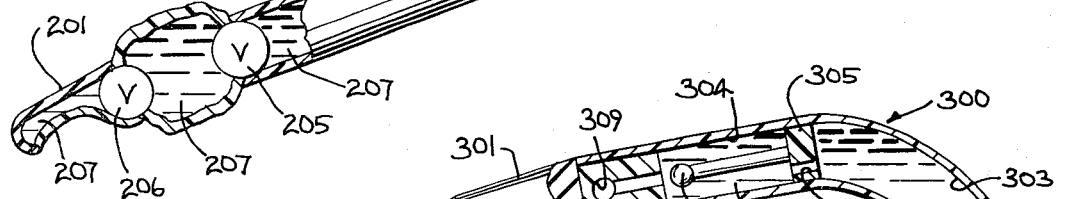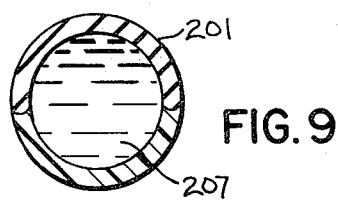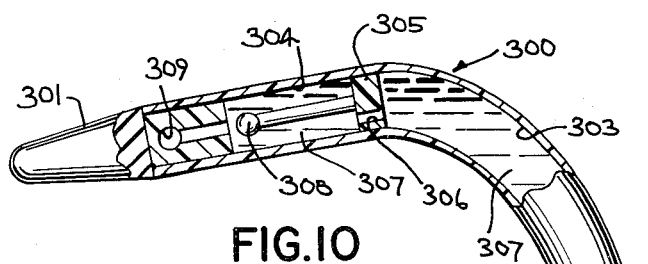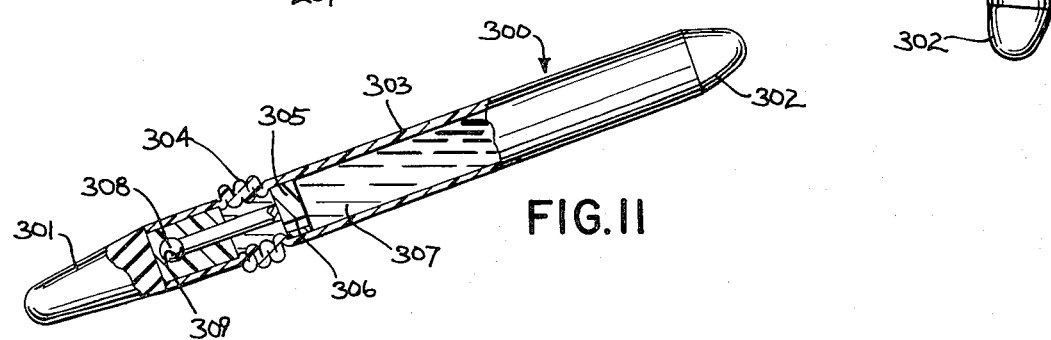

PENILE PROSTHESIS

This is a division of application Ser. No. 150,231, filed May 15, 1980, now U.S. Pat. No. 4,318,396.

The present invention relates to a penile prosthesis. More particularly, it relates to a penile prosthesis which is adapted to be implanted in man for treatment of erectile impotence.

BACKGROUND OF THE INVENTION

There are instances of erectile impotence in which the patient does not respond to more conventional therapy and the surgical implanting of a penile prosthesis may be the only practical means of remedying the impotency.

Several types of penile prostheses have been employed in the past. One type of penile prosthesis is a pair of rods of suitable stiffness which are surgically implanted into the corpus cavernosum of the penis. One disadvantage of some of the rod-type implants is the permanent stiffness of the rod which can be a source of physical pain and/or embarrassment to the patient. The prostheses disclosed in U.S. Pat. No. 3,893,476 and U.S. Pat. No. 4,066,037 are representatives of the rod type prostheses.

Another type of penile prosthesis which is available is the inflatable prosthesis. The most common inflatable prosthesis includes two fairly long inflatable and distensible tubes that are surgically implanted in the corpus cavernosum of the penis. Each of the two tubes is connected by tubing to a pressure bulb of inflating fluid which is implanted elsewhere in the body. Because of the volume required to inflate, distend, pressurize and rigidize the inflatable tubes, the pressure bulbs are relatively large. The prostheses of U.S. Pat. No. 3,954,102 and U.S. Pat. No. 4,009,711 are representative of the inflatable type prostheses.

SUMMARY OF THE INVENTION

It is the general object of the present invention to disclose a new type of penile prosthesis.

The penile prosthesis of the present invention comprises a pair of penile implants. Each of the implants is a flexible, elongated member having a short, relatively stiff proximal stem which is adapted to be implanted into the root end of the corpus cavernosum to support the implant and an elongated flexible, non-distensible distal portion having a chamber substantially filled with a non-compressible fluid and a conical tip. The distal portion is adapted to be implanted in the corpus cavernosum of the pendulus penis with the conical tip in the distal end of the corpus cavernosum. The implant also includes means for completely filling and pressurizing the chamber to make rigid the non-distensible distal portion and to stiffen the penis. In one embodiment, the chamber is filled and pressurized by squeezing the chamber and reducing its volume and in another it is filled and pressurized by transferring additional fluid under pressure into the chamber.

The proximal stem of the implant is relatively stiff so that when it is implanted into the root end of the corpus cavernosum it will anchor and support the implant and the distal portion and tip of the implant are soft so as to cause a minimum of irritation to the tissue of the penis. The distal portion which contains the chamber substantially filled with non-compressible fluid is flexible and when not pressurized permits the pendulus penis to assume a normal flaccid position. The tip of the distal portion of the implant is paraboloidal in shape to fit the end of the corpus cavernosum, and to enhance the physiological compatibility of the implant.

The means for completely filling and pressurizing the chamber to make the non-distensible distal portion rigid and to effect an erection may be a clamp or other means for squeezing, compressing the chamber and reducing its effective volume or a valve or port which permits the chamber to be filled by the transfer of additional fluid under pressure into the chamber.

Further objects and advantages of the prosthesis of the present invention will become apparent from the drawings and the description of the preferred embodiment.

BRIEF DESCRIPTION OF THE DRAWINGS

FIG. 5 is a top plan view, partly in section, of another form of implant which can be used in the prosthesis of the present invention;

FIG. 6 is a cross sectional view taken along line 6—6 in FIG. 5;

FIG. 7 is a side view, partly in section, of an implant which can be used in a second embodiment of the prosthesis of the present invention;

FIG. 8 is a side view similar to FIG. 7 except that the implant is pressurized.

FIG. 9 is a cross sectional view taken along line 9—9 in FIG. 7;

FIG. 10 is a side view, partly in section, of another implant which can be used in the second embodiment of the present invention; and FIG. 11 is a side view similar to FIG. 10 except that the implant is pressurized.

DESCRIPTION OF THE PREFERRED EMBODIMENTS

Figure 1:
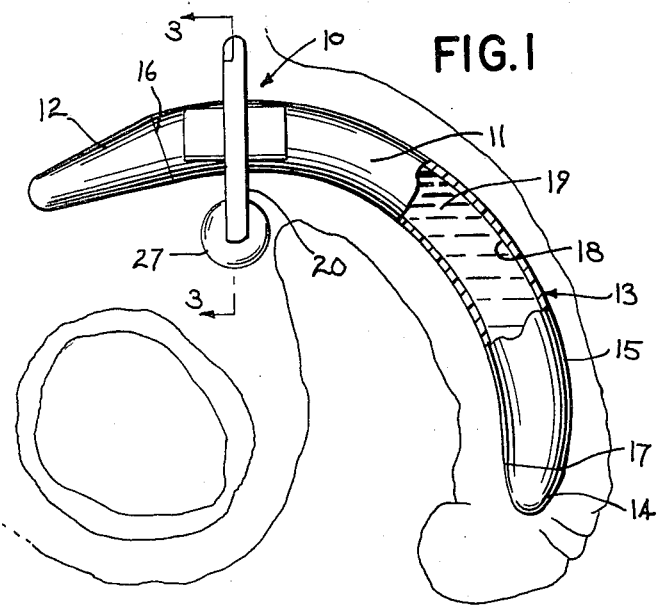
FIG. 1 is a side view, partly in section, of a penile prosthesis of the present invention in a non-pressurized condition surgically implanted in a male.
Figure 3:
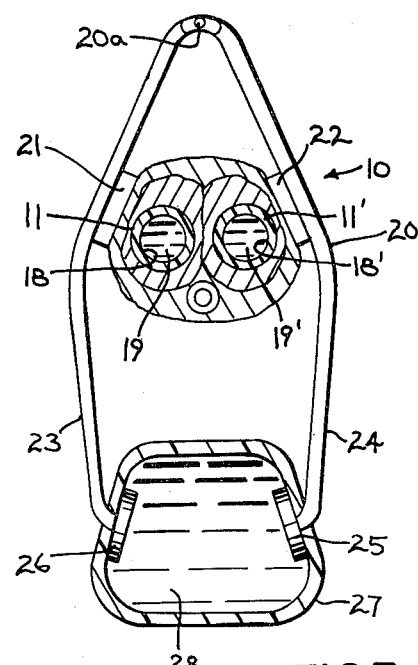
FIG. 3 is a cross sectional view taken along the line 3—3 in FIG. 1.
Figure 2:
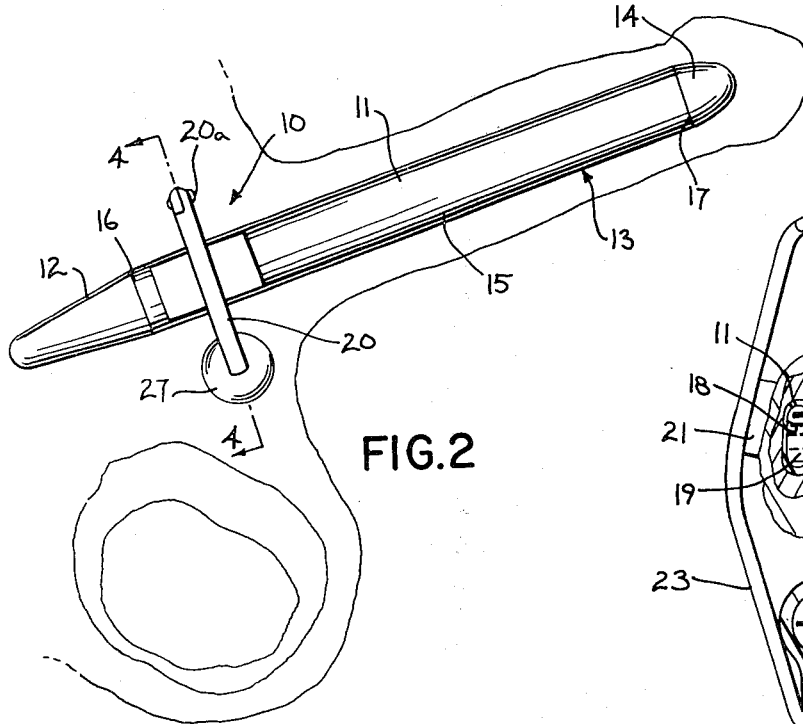
FIG. 2 is a side view similar to FIG. 1, except that the prosthesis is pressurized.
Figure 4:
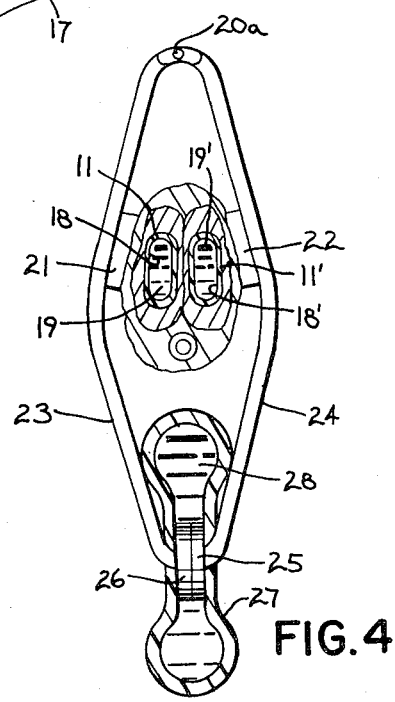
FIG. 4 is a cross sectional view taken along the line 4—4 in FIG. 2.

As seen in FIGS. 1-4, one embodiment of a penile prosthesis 10 comprises a pair of elongated cylindrical members 11, 11[1] of a physiologically inert material such as medical grade silicone rubber. The two implants 11, 11[1] are identical and only one will be described in detail. The implant 11 has a short, proximal stem 12 of relatively stiff material which is implanted in the root end of the corpus cavernosum to support and anchor the implant, an intermediate tubular portion 13, and a conical distal tip 14. The tubular portion 13 and the tip 14 are of soft, flexible material and they are implanted into the corpus cavernosum of the pendulus penis. The tip 14 is paraboloidal in shape to conform to the inner shape of the end of the corpus cavernosum. As seen in FIGS. 2 and 4, there are two implants 11, 11[1]. Each of the implants 11, 11[1] is implanted in a corpus cavernosum of the penis.

The intermediate tubular portion 13 of the implant 11 includes a tubular sleeve 15, preferably of a silicone coated mesh or woven fabric, which is sealed at its ends 16 and 17 to the stem 12 and tip 14, respectively, in a fluid-tight manner to form a cylindrical non-distensible chamber 18. The seals 16, 17 may be made with a suitable adhesive or by other conventional means. As seen in FIG. 1, in its non-pressurized state the chamber 18 is substantially filled with a non-compressible fluid 19, such as saline or a free flowing silicone gel.

Referring specifically now to FIGS. 1 and 3, it can be seen that when the chambers 18, $18^1$ containing the non-compressible fluid 19 are not pressurized, the soft, flexible, non-distensible, intermediate tubular portion 13 of the member 11 permits the penis to assume a substantially normal, flaccid position. However, when as seen in FIG. 2 the chambers 18, $18^1$ are filled and pressurized, they cause the penis to assume an erectile position.

As seen in FIGS. 1 to 4, a clamp 20 is implanted in an operative position about the prosthesis 10. When the clamp 20 is open, as in FIG. 2, it exerts no compressive force on the chambers 18, $18^1$, but when it is closed as in FIG. 4 the clamp 20 squeezes or exerts a compressive force on the chambers 18, $18^1$ and the fluid 19, $19^1$ thereby reducing the effective internal volume of the chambers 18, $18^1$ and causing the implants 11, $11^1$ and penis to assume the pressurized erectile position seen in FIG. 2.

Referring now to FIGS. 3 and 4, it can be seen that the clamp 20 is basically a modified C clamp with a compressive pad 21, 22 positioned intermediate the length of each arm 23, 24. The arms 23 and 24 are hinged together at one end, respectively, by a hinge pin 20a and the other ends of the arms 23, 24 are provided with magnets 25 and 26 of opposite polarity which are attracted to each other. The hinge pin 20a is removable so that the clamp 20 can be disassembled for implanting and then reassembled.

As seen in FIG. 3, the pads 21 and 22 and the magnets 25 and 26 are normally maintained in a spaced apart position. However, when the magnets 25 and 26 are physically moved together they are retained in that position, as seen in FIG. 4, as a result of their magnetic attraction for each other. To facilitate opening the clamp 20, keeping it open, and preventing tissue from growing between the magnets 25, 26 and otherwise interfering with the operation of the clamp 20, the ends of the arms 23, 24 and the magnets 25, 26 are preferably enclosed in a flexible walled capsule 27 which may contain a fluid 28.

The chambers 18, $18^1$ of the implants 11, $11^1$ are filled and pressurized by manually forcing the magnets 25 and 26 of opposite polarity toward each other thus squeezing and compressing the walls of the chambers and reducing the effective volume of the chambers 18, $18^1$, so that they are completely filled and also exerting pressure on the fluid 19, $19^1$. Because of their magnetic attraction the magnets 25 and 26 do not normally return to their original position. When it is desired to depressurize the implants 11, $11^1$, the clamp 20 is opened by squeezing the fluid filled capsule 27. The fluid pressure thus generated forces the magnets 25 and 26 back to their original spaced apart relationship and helps maintain them in that position. If desired a spring (not shown) can be included in the hinge of the clamp 20 to assist in keeping the clamp 20 open.

The unique combination of the penile implants 11, $11^1$ which include the tubular non-distensible chambers 18, $18^1$ substantially filled with non-compressible fluid 19, $19^1$ and the clamp 20 for exerting pressure on the chambers 18, $18^1$ eliminates the need for separate bulbs of pressurizing fluid which were required with prior art inflatable penile prostheses.

A second embodiment of the invention which might be preferred for some uses is shown in FIGS. 5 and 6. As seen therein, an implant 100 comprises a unitary member having a pair of stems 101, $101^1$ at the distal end and a pair of tips 102, $102^1$ at the proximal end. The implant 100 has an intermediate non-distensible chamber 103 filled with fluid 104. As seen in FIG. 6, the chamber 103 is shaped to fit into the corpus cavernosum and is partitioned as at 105. The implant 100 may be combined with a clamp similar to that previously described or other means for squeezing the chamber 103 to provide a complete penile prosthesis.

Another second embodiment of the prosthesis of the present invention is shown in FIGS. 7 to 11. In the embodiment seen therein the non-distensible chamber is filled and pressurized by the transfer of additional fluid into a non-distensible chamber.

Referring now to FIGS. 7, 8 and 9, there can be seen an implant 200 with a stem 201 at the proximal end and a tip 202 at the distal end. Positioned intermediate the stem 201, which is hollow as seen in FIG. 9, and the tip 202 is a first bulbar chamber 203 and a second tubular non-distensible chamber 204. Fluid transfer between the chamber 203 and the second chamber 204 is controlled by a two-way valve 205. A second two-way valve 206 controls fluid flow between the stem 201 and the first chamber 203. As seen in FIG. 7, the hollow stem 201 and the chambers 203 and 204 are all substantially filled with a non-compressible fluid 207. When it is desired to pressurize the second non-distensible chamber 204, the bulbar chamber 203 is forcibly squeezed manually forcing fluid 207 under pressure through the valves 206 and 205 into the chamber 204, causing it to fill and stiffen and the stem 201 and chamber 203 to partially collapse as seen in FIG. 8. Upon release of the squeezing force, the valves 205 and 206 close. When it is desired to relieve the pressure in the chamber 204, the valves 205 and 206 are manually manipulated to an open position. In order to provide a complete penile prosthesis, two of the implants 200 are employed.

A large variety of different types of valves can be used as the valves 205 and 206 in the implant 200, including those disclosed in U.S. Pat. No. 4,009,711. Preferrably, the valves are of the type which open when the stem 201 or chamber 203 are squeezed, which close automatically when the squeezing stops and which can be opened by manipulation from the outside.

Another type of implant that can be used in the second embodiment of the invention is seen in FIGS. 10 and 11. The implant 300 as seen therein has a stem 301 at the distal end, a tip 302 at the proximal end and a pair of intermediate chambers 303 and 304 separated by a wall 305 having a port 306. As seen in FIG. 10 both chambers are substantially filled with a non-compressible fluid 307. The larger chamber 303 which is non-distensible is filled and pressurized to stiffen the distal portion of the implant 300 by manually moving the wall 305 toward the proximal stem 301 to transfer fluid 307 from the smaller chamber 304 into the chamber 303. As the wall 305 is moved, the smaller chamber 304 is emptied and collapses; it is held in the collapsed position seen in FIG. 11 by cooperation of the male member 308 and the female socket 309 which are manually engaged. When it is desired to depressurize the chamber 303, the male member 308 is manually disengaged from the female socket 309. Other locking means for holding the chamber 304 in the collapsed condition can be employed provided the means can be engaged and disengaged by manual manipulation from the outside. In order to provide a complete penile prosthesis, two of the implants 300 are employed.

The novel prosthesis of the present invention which has been described differs primarily from prior art inflatable prostheses in that the walls of the fluid containing chambers of the novel implants are non-distensible, i.e., they do not stretch or inflate. Other important differences are that the chambers even in the non-pressurized condition are substantially filled with non-compressible fluid so that relatively large separate pressure bulbs are not required to pressurize the chamber. If it is desired to use pressure bulbs to pressurize the substantially fluid filled non-distensible chambers of the implants of the present invention the bulbs need be of only minimal size.

The term "substantially filled" as used herein to described the fluid content of a chamber means that the chamber contains about 60% to about 95% or more of its capacity of a non-compressible fluid such as water, saline or a free flowing gel. The actual content of fluid can vary; however, the distal portion of the implant when "substantially filled" should be still sufficiently flexible so that the penis can assume a normal flaccid position.

All parts and components of the prosthesis are preferably made of or covered with medical grade silicone rubber which is non-reactive, non-toxic and well tolerated by the adjacent organic tissues. Silicone rubber is preferred because it is quite resistant to wear and tear and remains functional for long periods of time. However, other suitable materials possessing desirable properties also can be employed.

The sleeves which form the walls of the "non-distensible" chambers are preferably made of a mesh or fabric covered with silicone material so that they will not stretch when filled with fluid and excessive pressure will not be exerted on the tunica albuginea. The diameters of the sleeves are selected so that the implants fill the corpus cavernosum when the implants are in their pressurized state.

The proximal stems of the implants preferrably have a Shore A hardness of about 70, the distal tips a Shore A hardness of about 20, and each of the materials have sufficient tensile strength for its intended use.

The preferred method of implantation of the prosthesis is through an incision made at the penoscrotal junction. After appropriate incision, the corpus cavernosum is dilated distally and proximally to accept the implant. The appropriate anatomical measurements are made to insure that the proximal stem of a particular implant will be positioned at the base of the penis below the pelvic bone. An implant having an appropriately sized intermediate section and distal tip is inserted into the corpus cavernosum of the penis. The distal tip is positioned in the tunica end of the corpus cavernosum. The proximal stem of the implant then is anchored in the root end of the corpus cavernosum.

The identical procedure is performed on the other side of the penis to complete the surgical procedure. The proximal stems of the two implants preferably will diverge laterally to accommodate the anatomy and provide lateral stability to the penis. When the embodiment utilizing a clamp is employed, the clamp is implanted at the same time and the incision is then closed.

It will be apparent to those skilled in the art that use of the non-distensible chamber in the penile implant of the present invention permits the pressure in the chamber to be raised to the proper level with the least amount of fluid. Prior art prostheses employing distensible chambers need large amounts of fluids to pressurize to the proper level thus requiring large fluid reservoirs.

It is to be understood that the foregoing description has been for purposes of illustration and that a number of modifications and changes may be made without departing from the spirit and scope of the present invention. Therefore, the invention is not to be limited by any of the specific embodiments described but only by the claims which follow.

I claim:

1. A penile implant for use in a penile prosthesis comprises an elongated, flexible member of physiologically inert material having at one end a relatively short stem adapted to be inserted into the root end of the corpus cavernosum of a penis; a distal tip adapted to be implanted in the corpus cavernosum of the pendulous penis at the other end; a pair of axially aligned chambers intermediate said stem and said tip, the first of said chambers being collapsible and located adjacent the stem and the second of said chambers being non-distensible and located adjacent the tip, both of said chambers being substantially filled with liquid and separated by a dividing wall having an opening for communication between said chambers and locking means for holding said first chamber in a collapsed condition.

2. A penile implant of claim 1 in which the locking means for holding the first chamber in a collapsed condition consist of a pair of mating members, one on the dividing wall and the second on the interior opposing wall of the collapsible chamber.

3. A penile implant of claim 2 in which the mating members are a male member and a female socket.

* * * * *